(12) United States Patent
Hu et al.

(10) Patent No.: US 7,871,395 B2
(45) Date of Patent: Jan. 18, 2011

(54) CONDUIT MANAGEMENT SYSTEM

(75) Inventors: Yixin Hu, Montreal (CA); Teresa Mihalik, Montréal (CA); Cristian Petre, Laval (CA); Dan Wittenberger, L'Ile Bizard (CA)

(73) Assignee: Medtronic Cryocath LP, Toronto, Ontario (CA)

( * ) Notice: Subject to any disclaimer, the term of this patent is extended or adjusted under 35 U.S.C. 154(b) by 456 days.

(21) Appl. No.: 11/446,932

(22) Filed: Jun. 5, 2006

(65) Prior Publication Data

US 2007/0282256 A1 Dec. 6, 2007

(51) Int. Cl.
*A61M 29/00* (2006.01)
(52) U.S. Cl. .............. 604/96.01; 604/164.01; 604/164.13; 604/264; 604/523; 604/528; 604/915; 604/93.01
(58) Field of Classification Search .......... 604/96.01, 604/523, 102.02, 264, 93.01, 171, 159, 164.01, 604/102.01, 158, 164.13, 528, 164.09, 164.11, 604/915, 48; 242/364.9, 388.6
See application file for complete search history.

(56) References Cited

U.S. PATENT DOCUMENTS

| | | | |
|---|---|---|---|
| 3,561,445 A * | 2/1971 | Katerndahl et al. | 604/159 |
| 3,826,256 A | 7/1974 | Smith | |
| 4,151,648 A | 5/1979 | Hirth | |
| 4,160,451 A * | 7/1979 | Chittenden | 604/159 |
| 4,255,076 A | 3/1981 | Svenning | |
| 4,526,175 A | 7/1985 | Chin et al. | |
| 4,637,404 A | 1/1987 | Gessman | |
| 4,850,974 A * | 7/1989 | Bickelhaupt et al. | 604/171 |
| 5,064,415 A * | 11/1991 | Walder et al. | 604/164.02 |
| 5,800,393 A * | 9/1998 | Sahota | 604/103.07 |
| 5,855,567 A * | 1/1999 | Reesemann | 604/171 |
| 5,975,120 A | 11/1999 | Novosel | |
| 6,086,008 A * | 7/2000 | Gray et al. | 242/388.6 |
| 6,231,564 B1 * | 5/2001 | Gambale | 604/528 |
| 6,258,061 B1 * | 7/2001 | Drasler et al. | 604/131 |
| 6,334,457 B1 | 1/2002 | Baker, IV | |
| 6,569,158 B1 * | 5/2003 | Abboud et al. | 606/20 |
| 6,572,610 B2 | 6/2003 | Kovalcheck et al. | |
| 6,623,471 B1 * | 9/2003 | Barbut | 604/509 |

(Continued)

FOREIGN PATENT DOCUMENTS

EP 1398056 A1 3/2004

(Continued)

*Primary Examiner*—Kevin C Sirmons
*Assistant Examiner*—Shefali D Patel
(74) *Attorney, Agent, or Firm*—Christopher & Weisberg, P.A.

(57) ABSTRACT

The present invention may include a medical device having a handle, a catheter coupled to the handle, and an expandable element coupled to the catheter. The medical device may also include first and second elongate bodies that traverse a length of the handle and catheter. A housing may be disposed within the handle, wherein the housing defines a first opening able to receive a portion of the first elongate body, a second opening able to receive a portion of the second elongate body, and a third opening opposite the first and second openings able to receive a portion of both the first and second elongate bodies. A separation element may be disposed within the housing, with the separation element defining a path able to receive a portion of the second elongate body, and whereby a portion of the first elongate body forms a loop around the separation element.

18 Claims, 5 Drawing Sheets

U.S. PATENT DOCUMENTS

| | | |
|---|---|---|
| 6,682,473 B1 | 1/2004 | Matsuura et al. |
| 6,867,980 B2 | 3/2005 | Wrycraft |
| 6,936,042 B2 | 8/2005 | Wallace et al. |
| 2001/0056257 A1* | 12/2001 | Drasler et al. ............ 604/96.01 |
| 2002/0065512 A1 | 5/2002 | Fjield et al. |
| 2004/0006333 A1 | 1/2004 | Arnold et al. |
| 2006/0004286 A1 | 1/2006 | Chang et al. |

FOREIGN PATENT DOCUMENTS

| | | |
|---|---|---|
| WO | 0246080 A1 | 6/2002 |

* cited by examiner

CONDUIT MANAGEMENT SYSTEM

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention provides an apparatus for accommodating and managing lengths of conduit in a medical device.

BACKGROUND OF THE INVENTION

Medical devices used in surgery for performing ablation, dilation, and the like often include multiple conduits and connectors for providing both fluid flow and electrical connections between the device and a fluid supply and/or control console, as well as providing for steering or navigation of the device over a guidewire. In particular, some surgical procedures involve the expansion or inflation of an inflatable element, such as a balloon, which may be disposed on a catheter or similar device. The catheter may be inserted through the vasculature of a patient, applied directly to contact a tissue surface, etc. Regardless of the particular approach, the expansion/inflation of the balloon may result in alternating periods of slack and tension in the conduits providing fluid flow, electrical connections, and the like, which can cause axial and longitudinal movement of the conduits. Such movement may result in the undesired kinking and/or tangling of multiple conduits of a device, whereby the kinking may degrade or prevent the performance of the device, causing a reduction in the overall effectiveness and/or usability of the device for certain medical procedures.

In light of the above, it is desirable to provide for an apparatus for accommodating and managing lengths of conduit in a medical device to prevent unwanted kinking and/or damage to components, while further facilitating and easing overall use of the device.

SUMMARY OF THE INVENTION

The present invention advantageously provides a method and system for accommodating and managing lengths of conduit in a medical device to prevent unwanted kinking and/or damage to components, while further facilitating and easing overall use of the device.

In particular, the present invention provides a medical device having a handle, a catheter coupled to the handle, and an expandable element coupled to the catheter. The medical device may also include a first conduit, such as a fluid supply conduit in communication with the expandable element, wherein the first conduit traverses a length of the handle and catheter. A second conduit, such as a guidewire, may also traverse a length of the handle and catheter. In addition, a housing may be disposed within the handle, where the housing defines a first opening able to receive a portion of the first conduit, a second opening able to receive a portion of the second conduit, and a third opening opposite the first and second openings, such that the third opening is able to receive a portion of both the and second conduits. The present invention may further include a separation element disposed within the housing, with the separation element defining a channel able to receive a portion of the second conduit, and whereby a portion of the first conduit forms a loop around the separation element. In addition, the separation element may be rotatably coupled to the housing as to provide a reel of reserve conduit length that may dispensed upon experiencing a tension along the length of the conduit.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
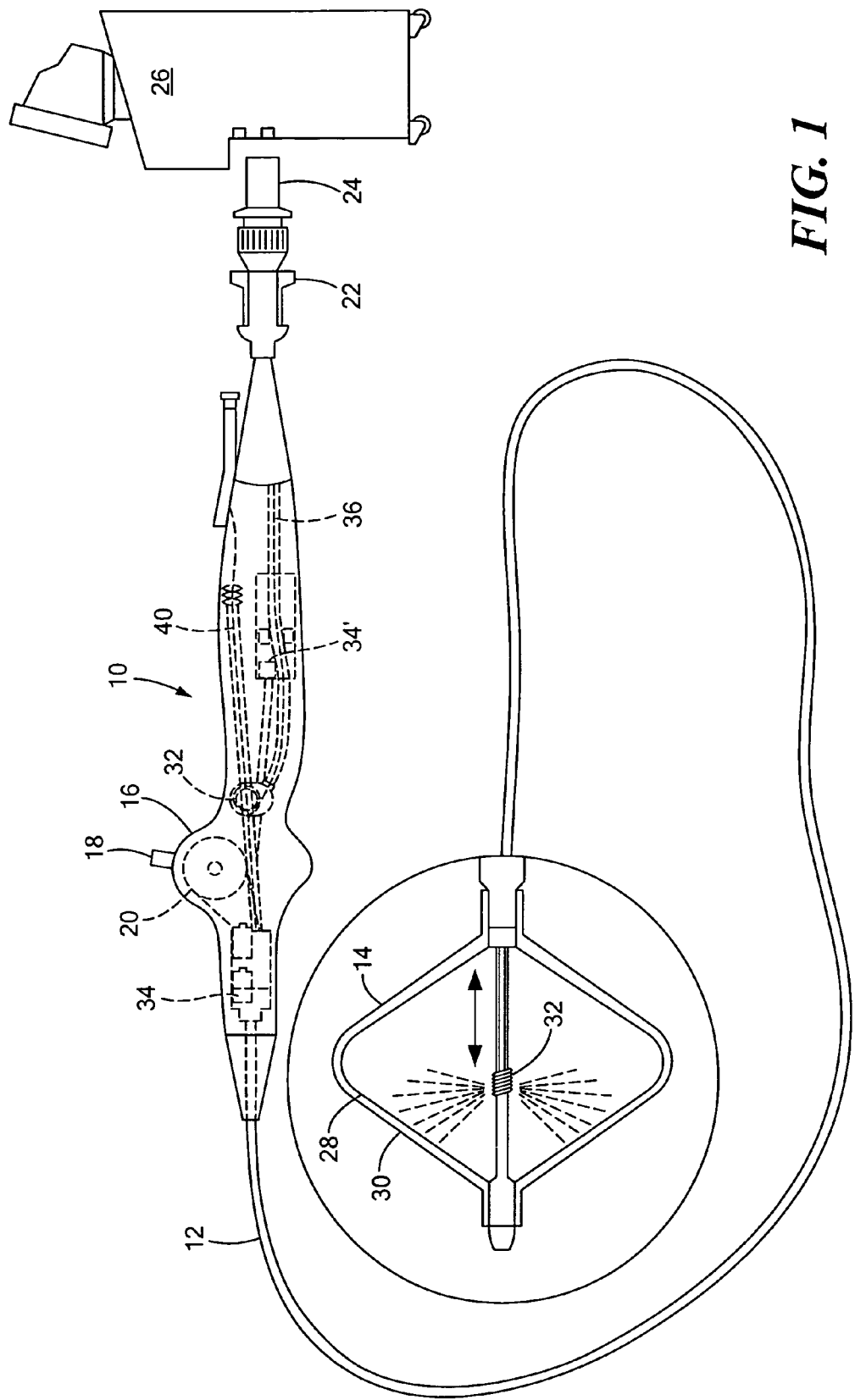
FIG. 1 illustrates a catheter system in accordance with an embodiment of the present invention.

FIG. 1 illustrates an exemplary system for performing a surgical procedure, including ablation, dilation, or the like. The system includes a medical device 10, which may include an elongate, highly flexible catheter 12 that may be suitable for passage through the vasculature. The catheter 12 may include a catheter body having a distal end with an expandable element 14 at or proximal to the distal end. The distal end and the expandable element 14 are shown magnified and are described in greater detail below. The catheter 12 body has a proximal end that is mated to a handle 16, where the handle 16 may include an element such as a lever or knob 18 for manipulating the catheter 12 body and the expandable element 14. In an exemplary embodiment, a pull wire with a proximal end and a distal end may have its distal end anchored to the catheter 12 at or near the distal end. The proximal end of the pull wire may be anchored to an element such as a cam 20 in communication with and responsive to the lever 18. The handle 16 can further include circuitry for identification and/or use in controlling of the ablation catheter 12 or another component of the system.

Continuing to refer to FIG. 1, the medical device 10 can also include one or more elongate bodies disposed within a portion of the handle 16, which may further extend along a length of the catheter 12. As used herein, the term "elongate body" is used to describe any structure and/or element for transmitting, communicating, and or channeling fluid, electricity, mechanical force, or the like, and may include, but is not limited to, tubing, piping, wiring, cable, and/or fiber optic elements. The handle 16 may be provided with a fitting for receiving an elongate body such as a guidewire that is passed into a guide wire lumen. The handle 16 may also include connectors that are matable directly to a fluid supply/exhaust and control unit or indirectly by way of one or more umbilicals. In the system illustrated, the handle 16 is provided with a first connector 22 that is matable with a co-axial fluid umbilical (not shown) and a second connector 24 that is matable with an electrical umbilical (not shown) that can further include an accessory box (not shown). In an exemplary system, the fluid supply and exhaust, as well as various control mechanisms for the system are housed in a single console 26. In addition to providing an exhaust function for the catheter 12 fluid supply, the console 26 can also recover and/or re-circulate the fluid.

Still referring to FIG. 1, the expandable element 14 is shown as a double balloon having a first membrane 28 (e.g., inner balloon) contained or enclosed within a second membrane 30 (e.g., outer balloon), thereby defining an interface or junction between the first and second membranes. The second membrane 30 may provide a safeguard to prevent fluid from leaking out of the interior of the first membrane 28 and into the surrounding tissue should the first membrane 28 rupture or develop a leak. A fluid supply tube may be placed in fluid communication with the fluid supply in the console 26 is provided to transport fluid from one or more openings in the conduit within the first membrane 28 in response to console commands and other control input. A vacuum pump in the console may create a low-pressure environment in one or more conduits within the catheter 12 body so that fluid is drawn into the conduit(s), away from the inner balloon, and towards the proximal end of the catheter 12. The vacuum pump may also be in fluid communication with the interface or junction of the inner and the outer balloons so that any fluid that leaks from the inner balloon is contained and aspirated. Additionally, the handle 16 may include one or more pressure sensors 34,34' to monitor the fluid pressure within the medical device 10.

Figure 2:
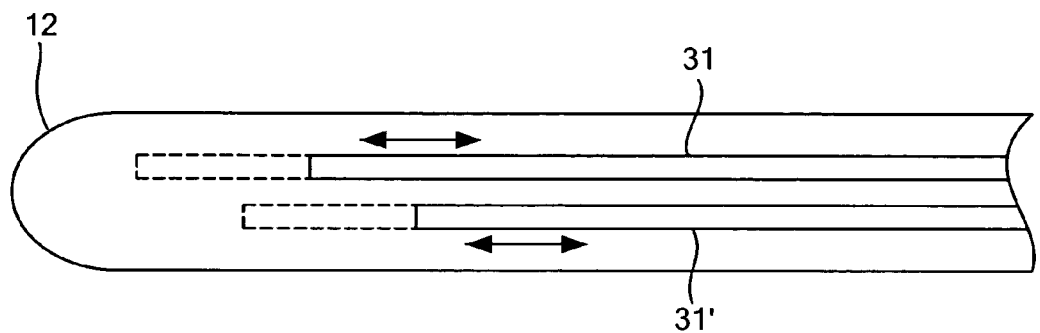
FIG. 2 provides a cross-sectional view of an embodiment of a medical device in accordance with the present invention.

An embodiment of a medical device in accordance with the present invention may alternatively include a distal tip absent any expandable or inflatable structure. For example, as shown in FIG. 2, the medical device 10 may include one or more elongate bodies 31,31' movably positioned within the catheter 12 in a desired configuration, with the elongate bodies potentially experiencing axial movement and/or changes in tension when the device is in use.

Figure 3:
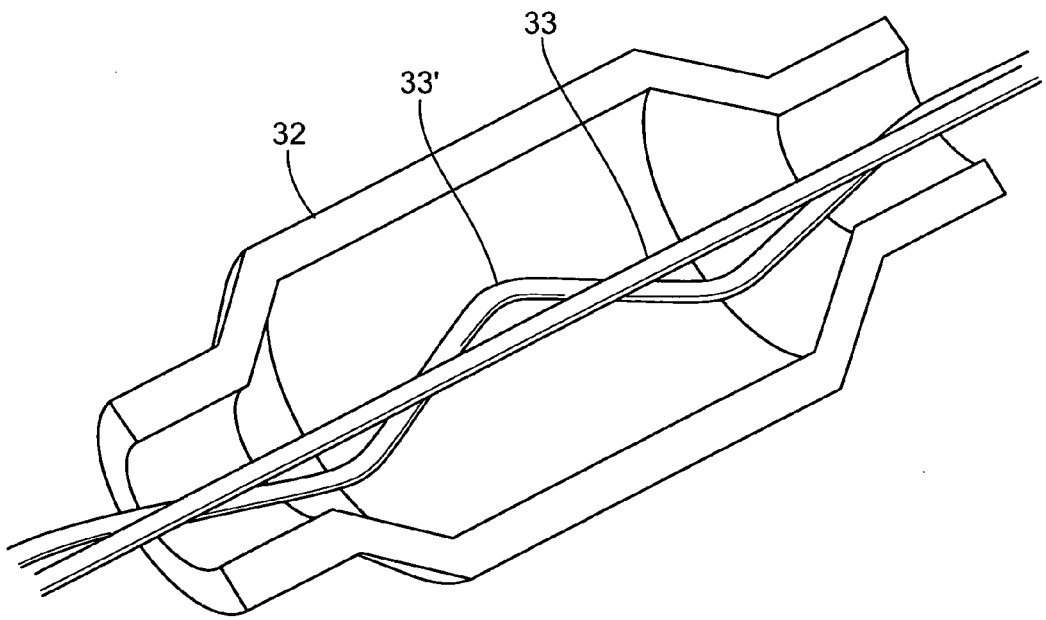
FIG. 3 provides another cross-sectional view of an embodiment of a medical device in accordance with the present invention.

Now referring to FIG. 3, the medical device 10 of the present invention may include a housing 32 for managing and accommodating lengths of one or more elongate bodies, including guidewires, fluid supply tubes, as well as other fluid, electrical, and/or mechanical tubing or wiring employed in the medical device 10. The housing may allow for the substantially unrestricted movement of one or more elongate bodies 33,33' by providing a cavity or interior space to accommodate excess lengths of the one or more elongate bodies. For example, the housing may have a larger inner diameter than other portions of the medical device 10. As such, should an elongate body at least partially disposed within the housing 32 experience some slack or other circumstance that causes the elongate body to retract or to "bunch up," the housing 32 provides room for the elongate body to do so while reducing the likelihood that the elongate body contacts an outer wall with such force as to cause kinking, bending, or other undesired results.

Figure 4:
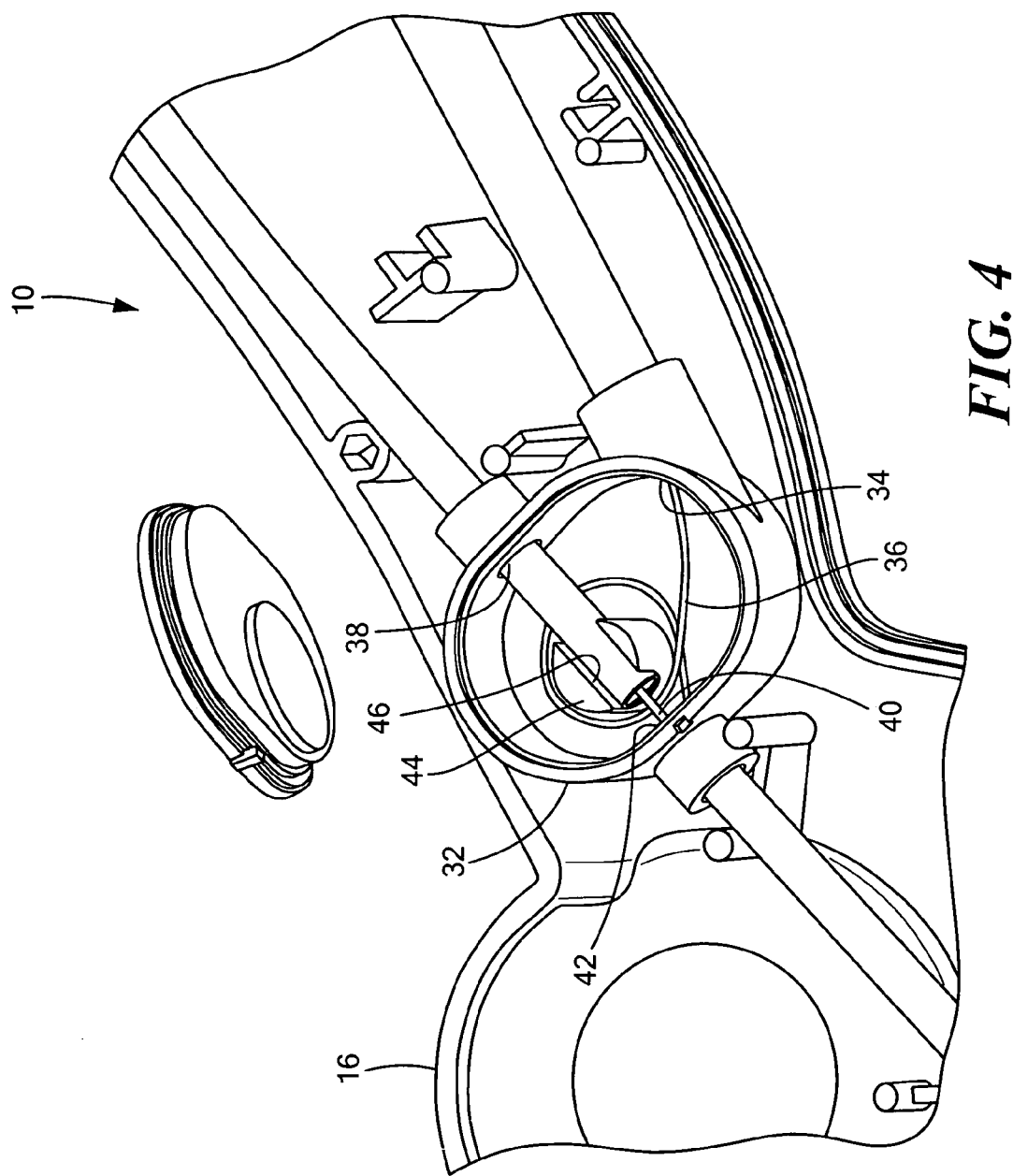
FIG. 4 shows an additional cross-sectional view of an embodiment of a medical device in accordance with the present invention.
Figure 5:
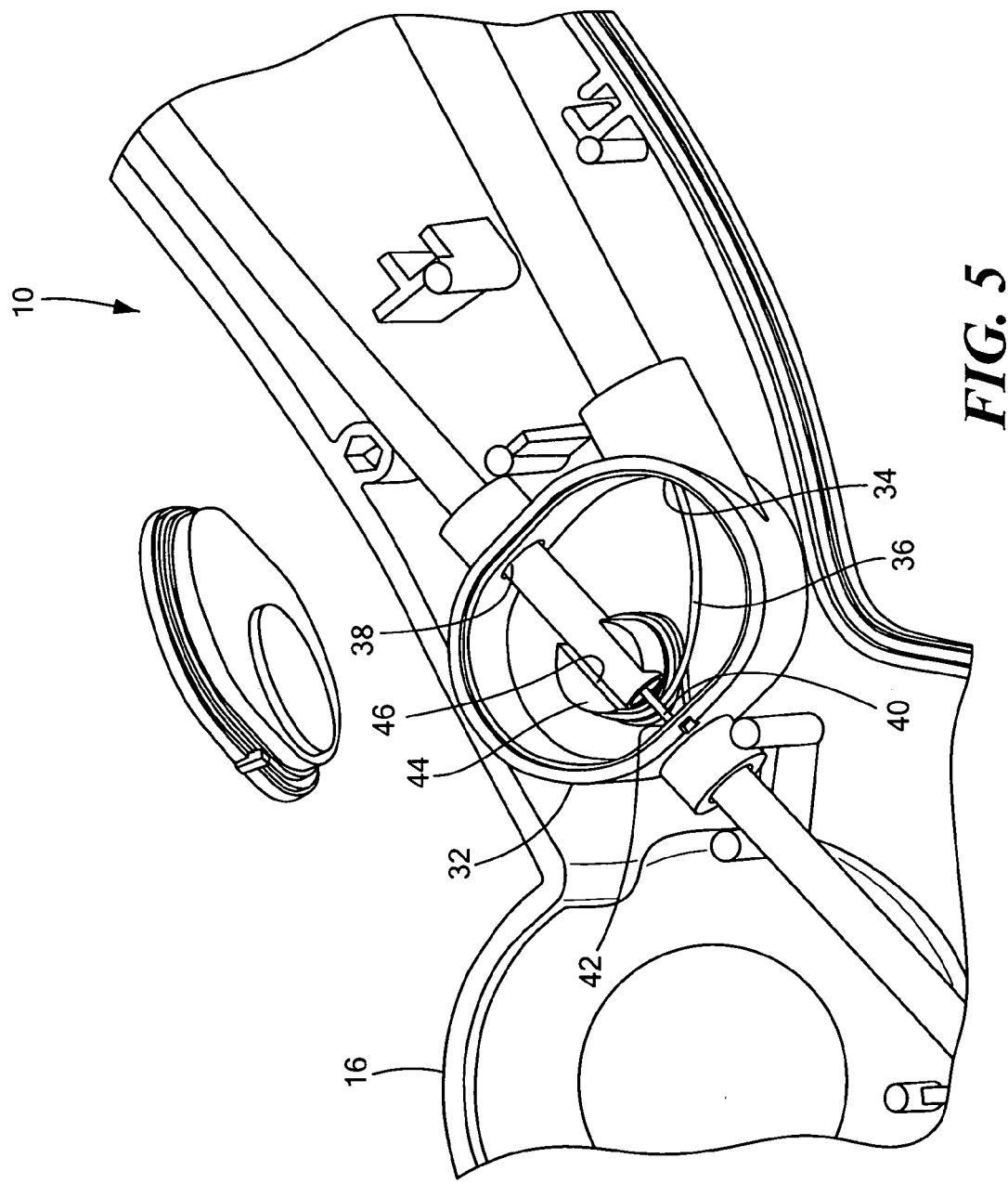
FIG. 5 shows yet another cross-sectional view of an embodiment of a medical device in accordance with the present invention.

Now referring to FIGS. 4 and 5, the medical device 10 of the present invention may include a housing 32 having a substantially rounded shape. The housing 32 may be disposed within the handle 16, and may include a first opening 34 for receiving a first elongate body 36, such as a portion of the fluid supply tube as well as a second opening 38 for receiving a second elongate body 40, such as a portion of the guidewire. The first and second openings 34,38 may receive portions of the first and second elongate bodies 36,40 from a proximal end of the handle. The housing 32 may further define a third opening 42 opposite the first and second openings for routing the first and second elongate bodies toward the distal end of the handle and towards the catheter 12 body. Although not shown, the housing 32 may include numerous additional openings for routing and/or managing additional lengths of elongate bodies disposed within the medical device 10.

A separation element 44 may be disposed within the housing 32, such that a portion of the first elongate body 36 may be wrapped around the separation element 44 prior to exiting the housing 32 through the third opening 42. The separation element 44 increases the likelihood that a portion of the first elongate body 36 remains in a looped-orientation such that tension or axial movement experienced by the first elongate body 36 does not cause the first elongate body 36 to kink or otherwise bend at an undesirable angle. For example, the separation element 44 may include a post or other structure having a width, thereby maintaining a spacing or diameter of the looped portion of the first elongate body 36. The width of the separation element 44 may be larger than a minimum bend or kink radius of the first elongate body 36, which may depend on the particular material from which the first elongate body 36 is constructed.

In addition, the separation element 44 may include a path 46 for receiving a portion of the second elongate body 40, thereby guiding the second elongate body 40 towards the third opening 42. The path 46 may be displaced from a portion of the separation element 44 about which the first elongate body 36 is looped around, thereby providing a spacing between the first and second elongate bodies within the housing 32. The path 46, for example, may include a channel, groove, depression, aperture or similar passage in the body of the separation element 44. Although not shown, the separation element may include multiple paths for additional elongate bodies coupled to the medical device to aid in managing and routing multiple elongate bodies through the length of the medical device to reduce the likelihood of tangling, kinking, or the like.

Moreover, a portion of the separation element 44 may be rotatably coupled to the housing 32 upon which lengths of an elongate body may be wound as to provide a reel of reserve elongate body length, as shown in FIG. 5. Upon experiencing tension along the first elongate body, the separation element 44 may rotate, thereby dispensing additional lengths of an elongate body as needed. The separation element 44 may further include a biasing element (not shown) such as a spring or other mechanism as known in the art, such that the separation element 44 automatically takes up additional slack by rotating and thus winding excess lengths of an elongate body about the separation element 44 when there is a reduced amount of tension experienced along the conduit length.

Figure 6:
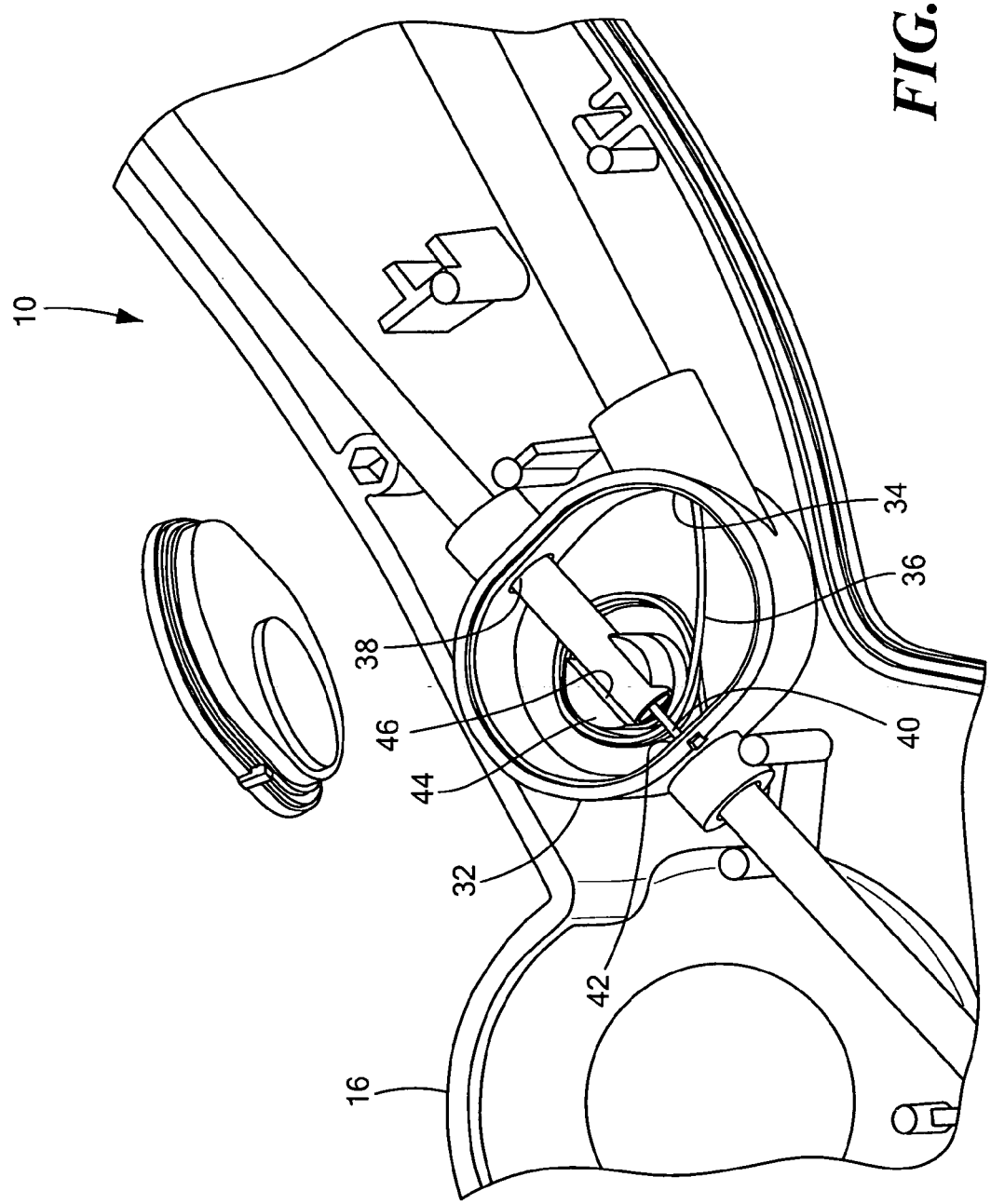
FIG. 6 provides an additional cross-sectional view of an embodiment of a medical device in accordance with the present invention.

In an exemplary use of the medical device 10 of the present invention during a medical procedure, the first elongate body 36, such as a fluid supply tube, is routed into the housing 32 through the first opening 34 to form a loop around the separation element 44, and subsequently directed out of the housing and towards the distal end of the catheter 12 through the third opening 42. In addition, the second elongate body 40, such as a guidewire, is routed through the second opening 38 of the housing 42, directed through the channel 46 of the separation element 44, and directed out of the housing 32 and towards the distal end of the catheter 12 through the third opening of the housing 42. During the medical procedure, should the first elongate body 36 experience an axial movement and/or a change in tension, for example, due to inflation of a balloon or similar structure, the slackened length of the elongate body will be taken up in the looped-portion of the conduit in the housing 32, i.e., an increase in the diameter of the looped portion will occur as shown in FIG. 6, thereby preventing kinking, as well as reducing any excess force on the medical device 10 that may cause a shift in positioning. Alternatively, should the separation element 44 be rotatably coupled to the housing, the slackened length of the elongate body may be taken up by rotating the separation element 44 either automatically or manually, as described above. Should the housing include a substantially rounded shape, the first expanded loop-portion of the first elongate body may expand to a width of the housing without contacting an angled surface which could cause kinking or bending of the first elongate body. In addition, the separate inlet portions of the housing 32 allow for separate and independent routing of the first and second elongate bodies, allowing for ease of connectability and manipulation of the individual elongate bodies and their connection points to the console 26, for example.

Although an embodiment of a medical device in accordance with the present invention has been discussed and illustrated as possibly including an expandable or inflatable element, such as a balloon, it is intended and contemplated that elements of the present invention may be suitable for use in any device having one or more elongate bodies that may experience an axial movement or change in tension during use.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A catheter, comprising:
a catheter body,
a housing coupled to the catheter body,
a separation element having a width disposed within the housing,
a first elongate body at least partially disposed within the catheter body and forming a loop around at least a portion of the separation element, and
a second elongate body at least partially disposed within the catheter body and at least partially disposed within the housing, wherein the separation element defines a path able to receive a portion of the second elongate body.

2. The catheter according to claim 1, wherein the second elongate body is a guidewire.

3. The catheter according to claim 1, wherein the housing defines a first opening receiving a portion of the first elongate body, a second opening receiving a portion of the second elongate body, and a third opening opposite the first and second openings, wherein the third opening receives a portion of both the first and second elongate bodies.

4. The catheter according to claim 1, wherein the separation element is a post.

5. The catheter according to claim 4, wherein the post is substantially cylindrical.

6. The catheter according to claim 1, wherein the first elongate body has a minimum bend radius, and the width of the separation element is greater than the minimum bend radius.

7. The catheter according to claim 1, wherein at least a portion of the separation element is rotatable with respect to the housing.

8. The catheter according to claim 1, further comprising a handle, wherein the housing is disposed within the handle.

9. The catheter according to claim 8, wherein the catheter body is coupled to the handle.

10. The catheter according to claim 9, further comprising an expandable element coupled to the catheter body.

11. The catheter according to claim 10, wherein the first elongate body is a fluid supply conduit in fluid communication with the expandable element.

12. The catheter according to claim 1, wherein the housing has a substantially rounded shape.

13. The catheter according to claim 1, further comprising a console in communication with one of the first and second elongate bodies.

14. A medical device, comprising:
a handle,
a catheter body attached to the handle;
a substantially rounded housing disposed within the handle,
a first elongate body at least partially disposed within the housing and at least partially disposed within the catheter body, the first elongate body forming a loop within the housing, and
a second elongate body partially disposed within the housing, wherein the housing defines a path able to receive a portion of the second elongate body.

15. The medical device according to claim 14, further comprising an expandable element coupled to the catheter body.

16. The medical device according to claim 15, wherein the first elongate body is a fluid supply conduit traversing a length of the catheter body and in fluid communication with the expandable element.

17. A medical device, comprising:
a handle;
a catheter body extending from the handle;
an expandable element coupled to the catheter body;
a fluid supply conduit in communication with the expandable element, wherein the fluid supply conduit traverses a length of the handle and catheter body;
a guidewire traversing a length of the handle and catheter body;
a housing disposed within the handle, wherein the housing defines a first opening receiving a portion of the fluid supply conduit, a second opening receiving a portion of the guidewire, and a third opening opposite the first and second openings, wherein the third opening receives a portion of both the fluid supply conduit and the guidewire;
a separation element disposed within the housing, wherein the separation element defines a path receiving a portion of the guidewire, and wherein a portion of the fluid supply conduit forms a loop around the separation element.

18. The medical device according to claim 17, further comprising a console coupled to the handle.

* * * * *